US00PP29289P3

(12) United States Plant Patent
Vitten et al.

(10) Patent No.: US PP29,289 P3
(45) Date of Patent: May 15, 2018

(54) STRAWBERRY PLANT NAMED 'DRISSTRAWFIFTY'

(50) Latin Name: *Fragaria×ananassa*
Varietal Denomination: DrisStrawFifty

(71) Applicant: Driscoll's, Inc., Watsonville, CA (US)

(72) Inventors: Matthias D. Vitten, Aptos, CA (US); Raúl Fernández Sánchez, Huelva (ES); Carlos D. Fear, Aptos, CA (US); Katalin Pakozdi, Maidstone (GB)

(73) Assignee: DRISCOLL'S, INC., Watsonville, CA (US)

( * ) Notice: Subject to any disclaimer, the term of this patent is extended or adjusted under 35 U.S.C. 154(b) by 0 days. days.

(21) Appl. No.: 14/999,062

(22) Filed: Mar. 25, 2016

(65) Prior Publication Data

US 2017/0280603 P1 Sep. 28, 2017

(51) Int. Cl.
*A01H 5/08* (2018.01)

(52) U.S. Cl.
USPC ..... Plt./208

(58) Field of Classification Search
USPC ..... Plt./208
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 Lopez
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.
PP22,218 P2 11/2011 Ferguson
PP22,247 P2 11/2011 Ferguson
PP23,107 P2 10/2012 Ferguson et al.
PP23,148 P2 10/2012 Gilford et al.
PP23,377 P2 2/2013 Ferguson et al.
PP23,378 P2 2/2013 Pullen et al.
PP23,382 P2 2/2013 Ferguson et al.
PP23,383 P2 2/2013 Ferguson et al.
PP23,400 P2 2/2013 Ferguson et al.
PP23,401 P2 2/2013 Pullen et al.
PP23,459 P2 3/2013 Stewart et al.
PP23,506 P3 4/2013 Ferguson et al.
PP23,517 P3 4/2013 Ferguson et al.
PP24,096 P3 12/2013 Fear et al.
PP24,317 P3 3/2014 Ferguson et al.
PP24,333 P3 3/2014 Vitten et al.
PP24,395 P3 4/2014 Vitten et al.
PP24,533 P3 6/2014 Ferguson et al.
PP24,745 P2 8/2014 Vitten et al.
PP25,408 P3 4/2015 Vitten et al.
PP25,437 P3 4/2015 Vitten et al.
PP25,698 P3 7/2015 Ferguson et al.
PP25,699 P3 7/2015 Stewart et al.

| | | | |
|---|---|---|---|
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| 2003/0079263 | P1 | 4/2003 | Gilford et al. |
| 2013/0276182 | P1 | 10/2013 | Fear et al. |
| 2016/0270276 | P1 | 9/2016 | Vitten et al. |
| 2016/0302339 | P1 | 10/2016 | Vitten et al. |

OTHER PUBLICATIONS

Ferguson et al., U.S. Appl. No. 14/545,992, filed Jul. 15, 2015 titled "Strawberry Plant Named Drisstrawfortyseven".

Kibbe et al, U.S. Appl. No. 14/756,125, filed Aug. 4, 2015 titled "Strawberry Plant Named Drisstrawfortyeight".

Kibbe et al., U.S. Appl. No. 14/545,991, filed Jul. 15, 2015 titled "Strawberry Plant Named Drisstrawfortynine".

*Primary Examiner* — Anne Marie Grunberg

(74) *Attorney, Agent, or Firm* — Morrison and Foerster LLP

(57) ABSTRACT

A new and distinct variety of strawberry plant named 'DrisStrawFifty' particularly characterized by having medium-sized, dark orange-red fruit, a globose-semi-upright plant habit, and mid-season harvest maturity, is disclosed.

2 Drawing Sheets

STRAWBERRY PLANT NAMED 'DRISSTRAWFIFTY'

Genus and species: *Fragaria×ananassa.*
Variety denomination: 'DrisStrawFifty'.

BACKGROUND OF THE NEW PLANT

The present invention relates to a new and distinct strawberry variety designated 'DrisStrawFifty' and botanically known as *Fragaria×ananassa*. This new strawberry variety was discovered in Huelva, Spain in March 2010, and originated from a cross between the proprietary female parent 'DrisStrawSixteen' (U.S. Plant Pat. No. 22,247) and the proprietary male parent 'RES 070-001' (unpatented). A single plant was selected and asexually propagated via tissue culture and vegetative cuttings in Huelva, Spain in 2010.

'DrisStrawFifty' underwent further testing in Doñana, Huelva, Spain from 2011-2015. The present invention has been found to retain its distinctive characteristics through successive asexual propagations via stolons and tissue culture.

SUMMARY OF THE INVENTION

The following are the most outstanding and distinguishing characteristics of this new cultivar when grown under normal horticultural practices in Huelva, Spain.

1. Medium-sized, dark orange-red fruit;
2. Globose-semi-upright plant habit; and
3. Mid-season harvest maturity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from six-month-old plants.

DESCRIPTION OF THE NEW VARIETY

Figure 1:
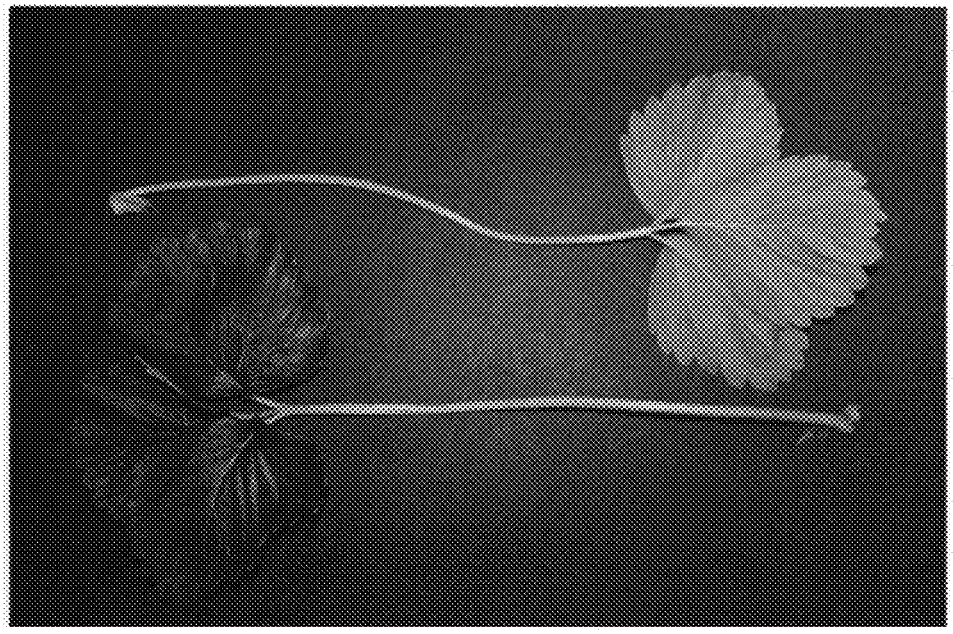
FIG. 1 shows upper and lower surfaces of the leaves of the plant with three leaflets.
Figure 2:
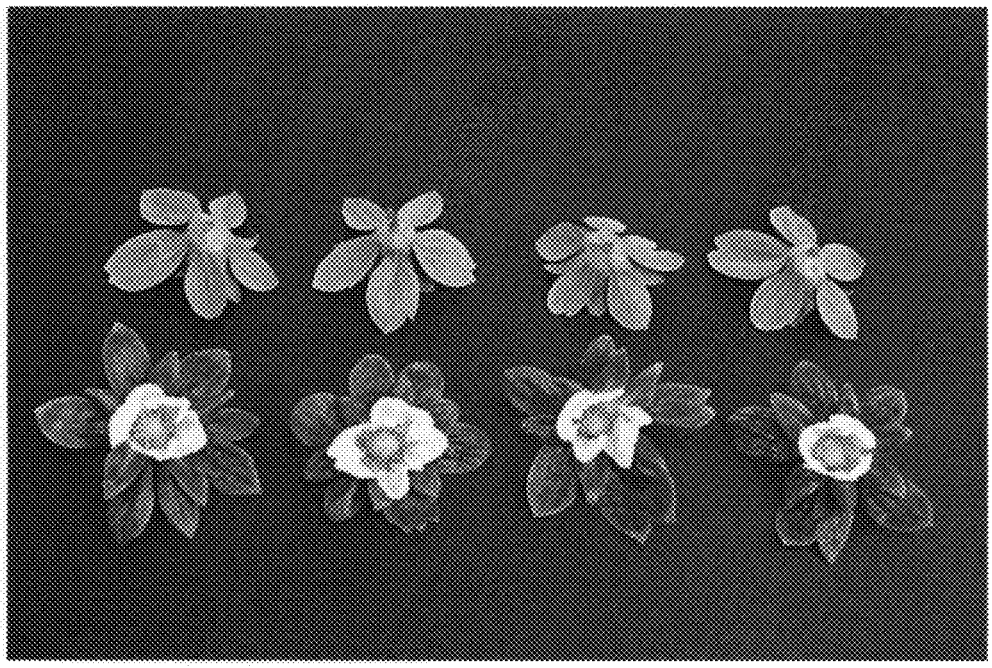
FIG. 2 shows both upper and lower surfaces of the flowers.
Figure 3:
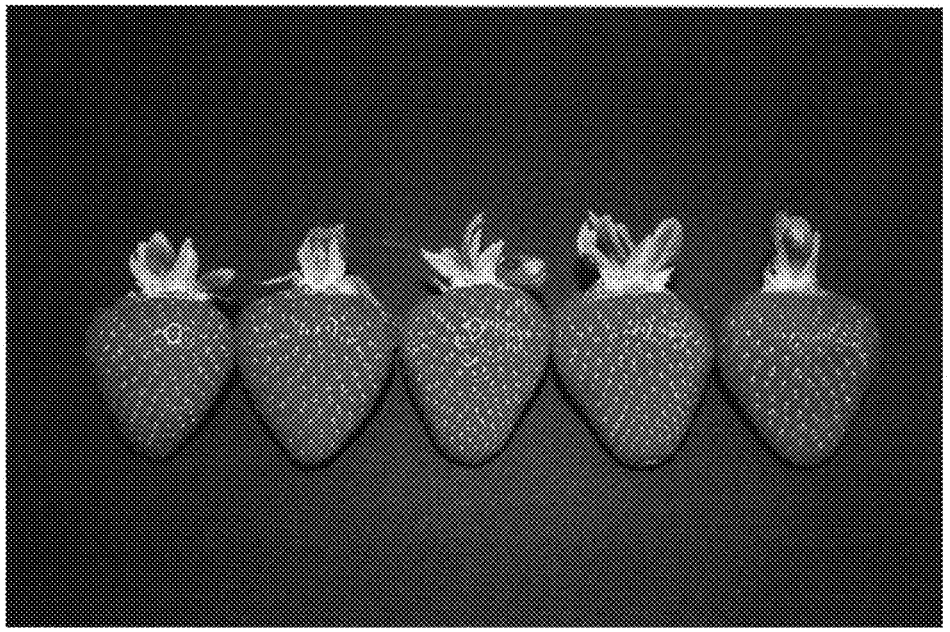
FIG. 3 shows the whole fruit.
Figure 4:
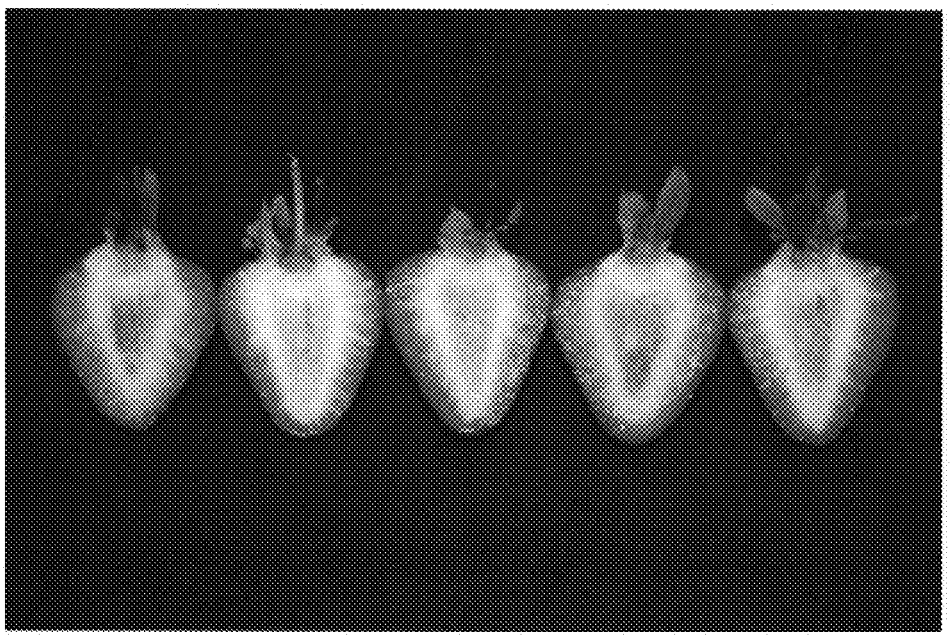
FIG. 4 shows the fruit in longitudinal cross-section.

The following detailed descriptions set forth the distinctive characteristics of 'DrisStrawFifty'. The data which define these characteristics is based on observations taken in Huelva, Spain from 2011 to 2015. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFifty' has not been observed under all possible environmental conditions. The botanical description of 'DrisStrawFifty' was taken from six-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:
- *Species.*—*Fragaria×ananassa.*
- *Common name.*—Strawberry.
- *Denomination.*—'DrisStrawFifty'.

Parentage:
- *Female parent.*—The proprietary variety 'DrisStrawSixteen' (U.S. Plant Pat. No. 22,247).
- *Male parent.*—The proprietary variety 'RES 070-001' (unpatented).

Plant:
- *Height.*—22.5 cm.
- *Diameter.*—35.4 cm.
- *Number of crowns/plant.*—3.
- *Habit.*—Globose — semi-upright.
- *Density of individual plant.*—Medium.
- *Vigor* (*health and hardiness of plant*).—Medium.

Terminal leaflets:
- *Size.*—Medium. Length: 7.2 cm. Width: 7.1 cm. Length/width ratio: 1.0 (As long as broad).
- *Number of teeth/terminal leaflet.*—21.
- *Shape of teeth.*—Obtuse — serrate to crenate.
- *Color.*—Upper surface: RHS N137B (Dark green). Lower surface: RHS 146B (Medium yellow-green).
- *Shape in cross section.*—Concave.
- *Blistering.*—Absent or very weak.
- *Glossiness.*—Medium.
- *Number of leaflets.*—Three only.
- *Shape.*—Orbicular.
- *Base shape.*—Rounded.
- *Apex descriptor.*—Rounded.
- *Margin.*—Crenate.
- *Margin profile.*—Involute (margins rolled inwards).
- *Variegation.*—Absent.

Petiole:
- *Length.*—Medium; 15.9 cm.
- *Diameter.*—3.30 mm.
- *Pubescence.*—Medium.
- *Pose of hairs.*—Slightly upwards.
- *Color.*—RHS 144C (Medium yellow-green).
- *Bract frequency.*—0.

Petiolule:
- *Length.*—9.60 mm.
- *Diameter.*—1.70 mm.
- *Color.*—RHS 145A (Medium yellow-green).

Stipule:
- *Length.*—3.7 cm.
- *Width.*—9.60 mm.
- *Pubescence.*—Medium.
- *Stipule anthocyanin coloration.*—Medium; RHS 145B (Medium yellow-green).

Stolon:
- *Number.*—Medium.
- *Average number of daughter plants per square foot.*—3.5.
- *Anthocyanin coloration.*—Strong; RHS 166A (Dark greyed-orange).
- *Diameter at bract.*—4.20 mm.
- *Thickness.*—Thin.
- *Density of pubescence.*—Sparse.

Inflorescence:
- *Position relative to foliage.*—Above.
- *Number of flowers per plant.*—Few.
- *Time of flowering* (50% *of plants at first flower*).—December.

*Flower size*.—Medium.

*Flower diameter*.—40.40 mm.

*Petals*.—Shape: Orbicular. Apex: Rounded. Base: Concavo-convex. Margin: Entire. Spacing: Overlapping. Length: 16.00 mm. Width: 15.60 mm. Length/width ratio: 1.0 (As long as broad). Petal number per flower: 5. Color (upper surface): RHS NN155C (White).

*Calyx*.—Diameter: 47.00 mm. Diameter relative to corolla: Larger. Insertion of calyx: Set above fruit — raised. Pose of calyx segments: Spreading — outwards. Size of calyx in relation to fruit: Slightly larger. Adherence of calyx: Medium.

*Sepal*.—Shape: Elliptical. Apex: Truncate. Margin: Entire. Length: 20.90 mm. Width: 10.70 mm. Sepal number: 10.

*Receptacle color*.—RHS 5B (Medium yellow).

*Stamen*.—Present. Anther color: RHS 153B (Medium yellow-green).

*Pedicel*.—Attitude of hairs: Slightly upwards.

Fruiting truss:

*Length*.—Medium; 22.8 cm.

*Diameter at base of truss*.—3.10 mm.

*Number of berries per fruiting truss*.—3.

*Attitude at first picking*.—Semi-erect.

*Color at base of truss*.—RHS 145C (Light yellow-green).

Fruit:

*Relative fruit size*.—Medium.

*Length*.—39.20 mm.

*Width*.—34.70 mm.

*Length/width ratio*.—1.1 (Longer than broad).

*Fruit hollow length*.—17.90 mm.

*Fruit hollow width*.—10.20 mm.

*Fruit hollow length/width ratio*.—1.8.

*Fruit hollow center* (*cavity*).—Medium.

*Fruit weight*.—25.5 g.

*Predominant fruit shape*.—Conical.

*Difference in shape between primary and secondary fruits*.—Slight.

*Evenness of fruit surface*.—Even or very slightly uneven.

*Fruit skin color*.—RHS N34A (Dark orange-red).

*Evenness of fruit color*.—Slightly uneven.

*Fruit glossiness*.—Weak.

*Achenes*.—Insertion of achenes: Above the surface. Coloration (sunward side of berry): RHS 144B (Medium yellow-green). Coloration (shaded side of berry): RHS 144C (Medium yellow-green). Number per berry: 260. Weight (weight of achenes divided by total # seed): 0.00058 g.

*Firmness of flesh* (*when fully ripe*).—Medium.

*Color of flesh* (*excluding core*).—RHS 44A (Dark red).

*Color of core*.—RHS 44C (Medium red).

*Evenness of flesh color*.—Even.

*Distribution of flesh color*.—Marginal and central.

*Sweetness*.—Average of 8.3 degree Brix when measured from January to May of 2017 in Rociana, Spain.

*Texture when tasted*.—Fine.

*Type of bearing*.—Not everbearing — not remontant.

*Harvest interval*.—Early February to mid-May.

*Harvest maturity*.—Mid-season.

*Production*.—698.0 grams per plant of marketable fruit.

Disease and pest resistance:

*Powdery mildew*.—Moderately resistant.

COMPARISON WITH PARENTAL AND COMMERCIAL VARIETIES

When 'DrisStrawFifty' is compared to the female parent 'DrisStrawSixteen' (U.S. Plant Pat. No. 22,247), 'DrisStrawFifty' produces globose-semi-upright plants with medium vigor, while the plants of 'DrisStrawSixteen' have a globose habit with strong vigor. Additionally, plants of 'DrisStrawFifty' produce a medium number of stolons with strong anthocyanin coloration, while 'DrisStrawSixteen' plants produce few stolons, with little or no anthocyanin coloration.

When 'DrisStrawFifty' is compared to the male parent 'RES 070-001' (unpatented), 'DrisStrawFifty' has slightly smaller fruit than 'RES 070-001'.

'DrisStrawFifty' differs from the commercial variety 'DrisStrawEight' (U.S. Plant Pat. No. 20,735), in that 'DrisStrawFifty' has medium-sized fruit that is dark orange-red in color with weak glossiness, whereas 'DrisStrawEight' has large fruit that is medium red in color with medium glossiness. Additionally, plants of 'DrisStrawFifty' have a globose-semi-upright habit, whereas plants of 'DrisStrawEight' have a globose habit.

We claim:

1. A new and distinct variety of strawberry plant named 'DrisStrawFifty', substantially as illustrated and described herein.

* * * * *